(12) United States Patent
Kai et al.

(10) Patent No.: US 6,433,695 B1
(45) Date of Patent: Aug. 13, 2002

(54) LIQUID SENSOR AND BODY FLUID LEAK SENSING DEVICE COMPRISING THE SAME

(75) Inventors: Kazuo Kai, Osaka; Shoichiro Fujino, Miyazaki; Ritsuo Ando, Miyazaki; Hiroshi Todoroki, Miyazaki, all of (JP)

(73) Assignees: Sanwa Newtech Co., Ltd.; Nipro Corporation, both of Osaka (JP)

( * ) Notice: Subject to any disclaimer, the term of this patent is extended or adjusted under 35 U.S.C. 154(b) by 0 days.

(21) Appl. No.: 09/601,622

(22) PCT Filed: Feb. 3, 1999

(86) PCT No.: PCT/JP99/00449

§ 371 (c)(1),
(2), (4) Date: Aug. 4, 1999

(87) PCT Pub. No.: WO99/40420

PCT Pub. Date: Aug. 12, 1999

(30) Foreign Application Priority Data

Feb. 4, 1998 (JP) ............................................. 10-061860
Jan. 6, 1999 (JP) ............................................. 11-001418

(51) Int. Cl.$^7$ ................................................. G08B 21/00
(52) U.S. Cl. ..................... 340/604; 73/73; 200/61.05
(58) Field of Search ............................. 340/573.5, 604, 340/539; 73/73; 200/61.04, 61.05; 600/372, 382

(56) References Cited

U.S. PATENT DOCUMENTS

| | | | | |
|---|---|---|---|---|
| 3,782,179 A | * | 1/1974 | Richards | 73/73 |
| 4,131,773 A | * | 12/1978 | Maham et al. | 200/61.05 |
| 4,513,608 A | * | 4/1985 | Cuming | 73/73 |
| 5,568,747 A | * | 10/1996 | Lloyd | 73/73 |

* cited by examiner

Primary Examiner—Thomas Mullen
(74) Attorney, Agent, or Firm—Kubovcik & Kubovcik (57) ABSTRACT

A body fluid leak sensing device adapted for correctly informing only a caretaker of a leak of body fluid. The sensing device is miniaturized so as to properly operate in any worn state. A liquid sensor applicable to the body fluid leak sensing device is disposable and highly sensitive to even a small amount of body fluid. A sensor (1) comprises a water absorber (11) formed of a porous material with a high electrical resistance and an insulating coating film (14) on which the ends (12a, 13a) of the electrodes (12, 13) are secured at its sides and spaced from each other in such a way that one end (11a) of the water absorber (11) is exposed. There are provided means for detecting leak of body fluid by measuring the resistance of the sensor (1) and means for informing according to the detection.

4 Claims, 11 Drawing Sheets

| Sensor | Response time | | | | |
|---|---|---|---|---|---|
| | 1st time | 2nd time | 3rd time | 4th time | 5th time |
| The invention | 25 sec | 17 sec | 21 sec | 15 sec | 13 sec |
| Substrate | 130 sec | 50 sec | 23 sec | 45 sec | 17 sec |

LIQUID SENSOR AND BODY FLUID LEAK SENSING DEVICE COMPRISING THE SAME

TECHNICAL FIELD

The present invention relates to a liquid sensing sensor and an apparatus for sensing leakage of body fluid using the same.

BACKGROUND ART

Recently, in developed countries, a decrease in birthrate and an increase in elderly population have proceeded with increasing speed and the problem of caring for the aged has become a social problem. In Japan, although various administrative efforts have been made upon forecasting the near future, they are insufficient yet so that it is an exigent task to make a society that is comfortable for elderly people to live in.

Under these circumstances, in facilities where a large number of aged persons who are bedridden or suffering from senile dementia are cared for, man-power on the side of the care provider and the facility remain to be maintained sufficiently yet and workers therein are forced to work hard. The same situation will exist in the case of caring for patients with a heavy handicap.

One of the causes for such heavy work is an exchange of diapers. The reason is that aged persons and patients are heavier in body weight than babies and heavy physical work is required for the exchange of diapers. Besides, many of those aged persons or patients who need diapers cannot recognize excretion by themselves or cannot inform of excretion and hence it is necessary to make patrols day and night to check it. In particular, aged persons have low anabiotic ability of the skin or the like so that other problems such as skin diseases will arise if excrement is left untreated for a long time. Accordingly, patrols have to be made frequently.

If there is a means which enables caregivers to immediately know that excretion has occurred, the above-described problem will be alleviated. Some conventional means are introduced in Kaoru Nishimura: "Care for incontinence" published by Chuo Hoki Shuppan (First edition 5th print, Dec. 1, 1992). These include a sensor having electrodes whose tips are separated from each other. The sensor is inserted between the body and the diaper and an apparatus for sensing incontinence connected to the sensor is attached to or arranged near the person under care. When excreted urine flows between the electrodes, current flows due to ionizing components such as salts contained in urine to activate the sensing apparatus and inform of the excretion by means of a buzzer or the like.

However, the apparatus for sensing incontinence has the following problems.
(1) Sensors once used must be subjected to treatment such as washing or sterilization before they can be utilized again. This has a contrary effect of requiring cost and labor.
(2) With the sensor having the above structure, a certain amount of urine must flow to the position of the sensor. However, with recent development of a paper diaper, most of the excreted urine is quickly absorbed in the inside of the diaper. As a result, sometimes the sensor cannot sense excretion when it has actually occurred.
(3) Both the sensing apparatus and sensor sometimes do not work normally, causing problems in the wearable state because of the movement of the person under care.
(4) Although it is by nature sufficient that only the caregiver knows of an excretion, information means such as a buzzer let others know it so that the person under care will feel nervous when the buzzer sounds.

Under the circumstances, the present invention has been made and it is an object of the present invention to provide a body fluid leakage sensing apparatus that is downsized so as to be adapted to any state of wearing and that accurately informs only the caregiver, and a liquid sensing sensor that is applied to the body fluid leakage sensing apparatus and senses a small amount of body fluid with high sensitivity and can be thrown away.

DISCLOSURE OF THE INVENTION

For this purpose, according to the present invention, a liquid sensing sensor comprises a water absorber made of a porous material having high electric resistance provided on a head of the sensor, at least two electrodes having respective tips arranged separate from each other through the water absorber but fixed to the water absorber respectively, and a coating means for covering the water absorber and the tips. That is, even a small amount of body fluid is allowed to permeate into the inside of a porous material from its exposed portion to thereby reduce the resistance between the electrodes due to ionization components, so that the liquid can be recognized.

A body fluid leakage sensing apparatus using the sensor comprises a sensor that is made of a liquid-permeable porous material and that changes its electric resistance by permeation of a body fluid into the inside thereof, a comparative circuit that is connected with the sensor and senses the leakage of body fluid by a change in the resistance, a transmitter circuit that sends body fluid leakage information from the comparative circuit to a communicator means, and a power source for initiating respective circuits.

Further, a body fluid leakage sensing apparatus comprising a sensor-side transmitter-receiver wearable on the body by a person who has a possibility of leaking body fluid and a communicator-side transmitter-receiver for wireless monitoring of the sensor-side transmitter-receiver, is characterized in that the sensor-side transmitter-receiver comprises a battery, a sensor that is made of a liquid permeable porous material and that changes its electric resistance by permeation of a body fluid into the inside thereof, a command receiving means for receiving a command from the communicator-side transmitter-receiver, a judgment means for measuring a resistance value of the sensor by the command, comparing the resistance value with a predetermined value, and judging a presence or absence of leakage of body fluid, and a data transmitting means for transmitting data obtained by the judgment means to the communicator-side transmitter-receiver, and is further characterized in that the communicator-side transmitter-receiver comprises a power source, a command transmitting means for transmitting the command to the sensor-side transmitter-receiver, a data receiving means for receiving the data from the sensor-side transmitter-receiver, a notifying means for notifying of the presence or absence of the leakage of body fluid, a recording means for recording the presence of the leakage of body fluid, a judgment means for judging the received data and actuating the notifying means and the recording means, whereby a presence or absence of the leakage of body fluid by wireless is monitored.

Accordingly, when a leakage of body fluid is sensed by the above-described sensor, the comparative circuit judges whether or not the change sensed is leakage of body fluid by a change in resistance and if a judgment is made that the leakage of body fluid is present, then the comparator circuit produces a signal and transmits the signal from the transmitter circuit to the notifying means outside, thereby notifying a third party of the leakage.

BEST MODE FOR CARRYING OUT THE INVENTION

As the basic construction, the apparatus of the present invention includes a liquid sensing sensor that reduces its resistance when a liquid to be sensed permeates into a part thereof and senses the liquid by application of current thereto as the sensor, a transmitter that recognizes the leakage of body fluid by a change in current due to the reduction in resistance and transmits results of the recognition, and a receiver that receives the transmitted results and communicates them as the sensing apparatus.

To realize high sensitivity sensing so that even a small amount of liquid can be sensed, the sensor comprises two electrodes and a porous material originally having high electric resistance separating and insulating the tips of the electrodes from each other, with a part of the porous material being exposed, so that a liquid capable of being conductive by ionization can flow in and permeate into the porous material resulting in an abrupt reduction in resistance, which enables application of current between the electrodes.

As the porous material, for example, ceramics formed by calcination are suitable since they are easy to form and they can be adjusted to have a desired standardized pore diameter. For example, mention may be made of calcined porous glass called "shirasu porous glass" formed by accumulating and calcining shirasu (white sand) (Japanese Patent No. 1504002). Use of this material makes it possible to produce a high sensitivity sensor of a simple construction at low costs so that throwaway type sensors can be obtained.

As the sensing apparatus, the above-described sensor is used. Its form may be a unidirectional form in which unidirectional transmission from a transmitter to a receiver occurs or a so-called bi-directional form in which both sides are provided with transmitter-receiver functions and a sensed signal is transmitted from the transmitter to the receiver and at the same time a command is transmitted from the receiver side to the transmitter side for controlling or the like. Details of each form will be described in respective examples which follow. As an outline, the sensor judges whether or not the sensed signal is that of the liquid to be sensed and signalizes it. At the same time, a signal for the discrimination of this signal from those signals relative to the type of apparatus and individual apparatus is outputted. These signals are transmitted by wireless means and received by a receiver arranged at a distant place. The received signals are converted to notifying means before a notification to the effect that the leakage of body fluid is sensed can be communicated.

Hereinafter, the present invention will be described by examples referring to the drawings.

EXAMPLE 1

In the instant example, description will be made on a sensor which is applicable to a sensing apparatus.

Figure 1:
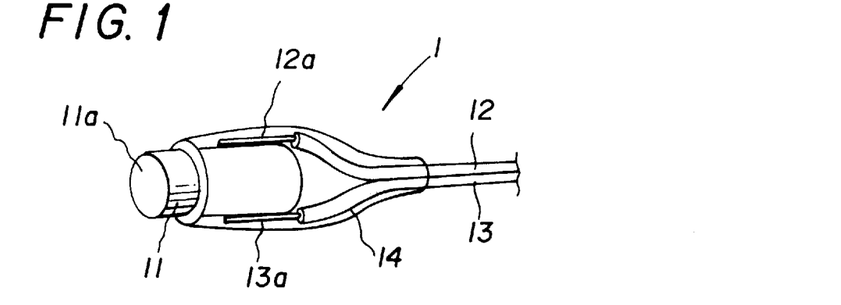
FIG. 1 is a perspective view showing the structure of the sensor of Example 1.

As shown in FIG. 1, a sensor 1 includes a water absorber 11 made of a porous material which has a high resistance value, electrodes 12 and 13 having tips 12a and 13a fixed on both side surfaces thereof and separated each other, and a coating 14 made of an insulating material, wherein the coating covers and fixes the tips and the water absorber so that an end 11a of the water absorber 11 is exposed. The water absorber 11 of the instant example is formed of shirasu porous glass formed by calcining as described above. The pore diameter of it is designed to a desired value in the range of 0.1 to 50.0 µm. After fixing the tips 12a and 13a, a heat-shrinking tube of an insulating material is used as the coating 14 to cover the tips and is heat-treated so as to fix it to the surface. Therefore, calcination of a large amount of water absorber 11 can reduce unit cost since the production process thereafter is easy. Covering with an insulating material can prevent unintended actuation due to static electricity from occurring.

The feature of the shirasu porous glass is that its pore diameter can be adjusted as designed by calcination. Therefore, water absorber 11 having a pore diameter most suited for sensors depending on the purpose and shape can be obtained.

Then, a brief explanation will be made of the method for producing the shirasu porous glass and properties thereof.

The production method is as follows. Lime or boric acid is added to shirasu and the mixture is melted at a temperature close to 1300° C. to form a basic glass based on CaO—$Al_2O_3$—$B_2O_3$—$SiO_2$. This is molded into a plate, tube, fiber, or bead depending on application. Then, the glass is heated again at a temperature in the range of 600 to 750° C. to cause micro phase separation into a glass rich in CaO and $B_2O_3$ and a glass rich in $Al_2O_3$ and $SiO_2$. Elution of the glass phase rich in CaO and $B_2O_3$ by acid treatment gives rise to a porous shirasu porous glass composed of the remaining $Al_2O_3$ and $SiO_2$ skeleton phase.

The obtained shirasu porous glass generally has a porous structure in which a number of penetrated holes of a uniformly controlled size are interconnected three-dimensionally, and its pore diameter can be designed freely within the range of from a superfine pore on the order of one millionth of 1 mm to a macropore on the order of one hundredth of 1 mm. The pores are of a cylindrical shape without a neck and have a large specific surface area.

The shirasu porous glasses have the following advantages.

As a crystal, they have high mechanical strength and are excellent in thermal resistance and durability. The compression deformation of the material is negligible even at high temperatures and at high pressures so that stable material properties can be maintained. It is easy to chemically modify their surface and organic functional groups can be introduced. They are excellent in resistance to chemicals except for strong alkalis and hydrofluoric acid and they are resistant to fungi and bacteria. They are easy to weld with each other or with other kinds of glasses. They are high in moldability and their shape can be designed so as to be suitable for the desired purpose.

The reason why shirasu porous glasses are used in the present invention is that they can easily absorb a liquid by capillarity and they have features that use of them allows a considerable change in the resistance between the electrodes due to ion conductivity of the liquid. The pore diameter of the shirasu porous glass may be selected appropriately in the range of 0.1 to 50 $\mu$m depending on the intended purpose. From the point of view of the response speed to detect urination, a pore diameter of 6 $\mu$m or more is desirable regardless of the diameter of the shirasu porous glass as will be shown in the following performance test results. Selection of suitable combinations of a plurality of shirasu porous glasses with different pore diameters enables selective absorption of only a body fluid that contains a molecule with a specified molecular weight from among body fluids excreted to detect and notify the leakage of target body fluid only.

Here, the respective results of performance tests of the sensor using shirasu porous glass will be explained below.

(1) Response Speed Test

The shirasu porous glass obtained by the above production method was tested for pore diameter-classified response speed on samples of the following standards.
1) Diameter: Three kinds (1 mm$\phi$, 1.5 mm$\phi$, 2 mm$\phi$)
2) Length: Three kinds (3 mm, 5 mm, 10 mm)
3) Pore diameter: Six kinds (0.86 $\mu$m, 3.0 $\mu$m, 6.8 $\mu$m, 10.9 $\mu$m, 13.6 $\mu$m, 17.0 $\mu$m)
4) Number of samples: 5 each
5) Composition of artificial urine:
   To 1 liter of water were added the following:
   Urea: 20.0g
   Sodium chloride: 8.0 g
   Magnesium chloride: 1.0 g
   Calcium chloride: 0.5 g
   Resistance 200 $\Omega$ (resistance of water: 700 $\Omega$)

Figure 2:
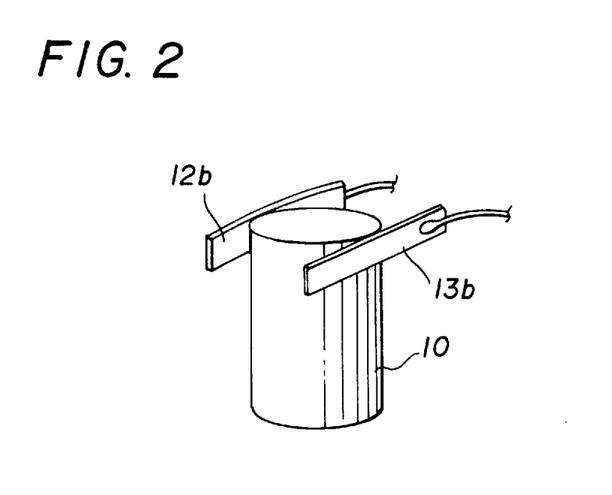
FIG. 2 is a perspective view showing the manner of testing a sample by the sensor.
Figure 3:
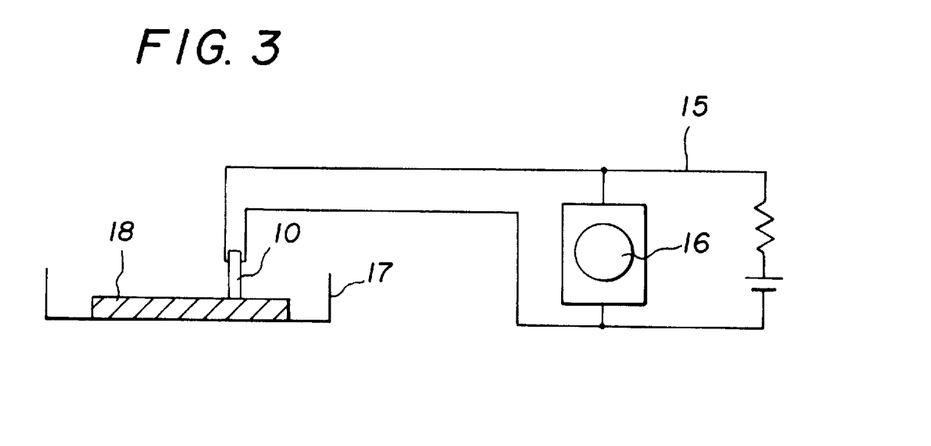
FIG. 3 is a schematic diagram showing the manner of testing a sample by the sensor.

The method of this test is as follows. As shown in FIG. 2, electrodes 12$b$ and 13$b$ connected to conductors, respectively, were attached to an upper part of a sample 10. The method of connecting the electrodes includes a method of pushing a metal piece onto shirasu porous glass directly and fixing it or by using sputtering, plating, conductive adhesive, solder that can adhere to glass or ceramic directly (for example, Serasolza (trade name) manufactured by ASAHI GLASS, Co., Ltd.).

Figure 4:
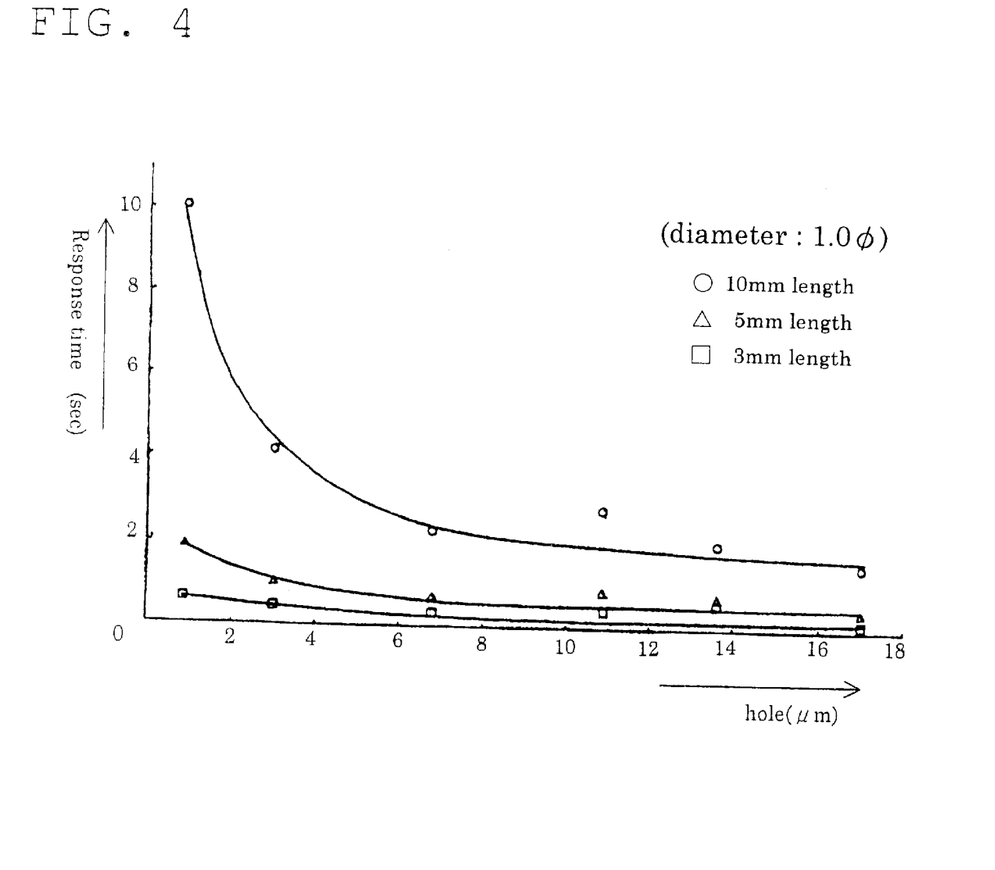
FIGS. 4, 5 and 6 are graphs each illustrating results of testing of a sample by the sensor.
Figure 5:
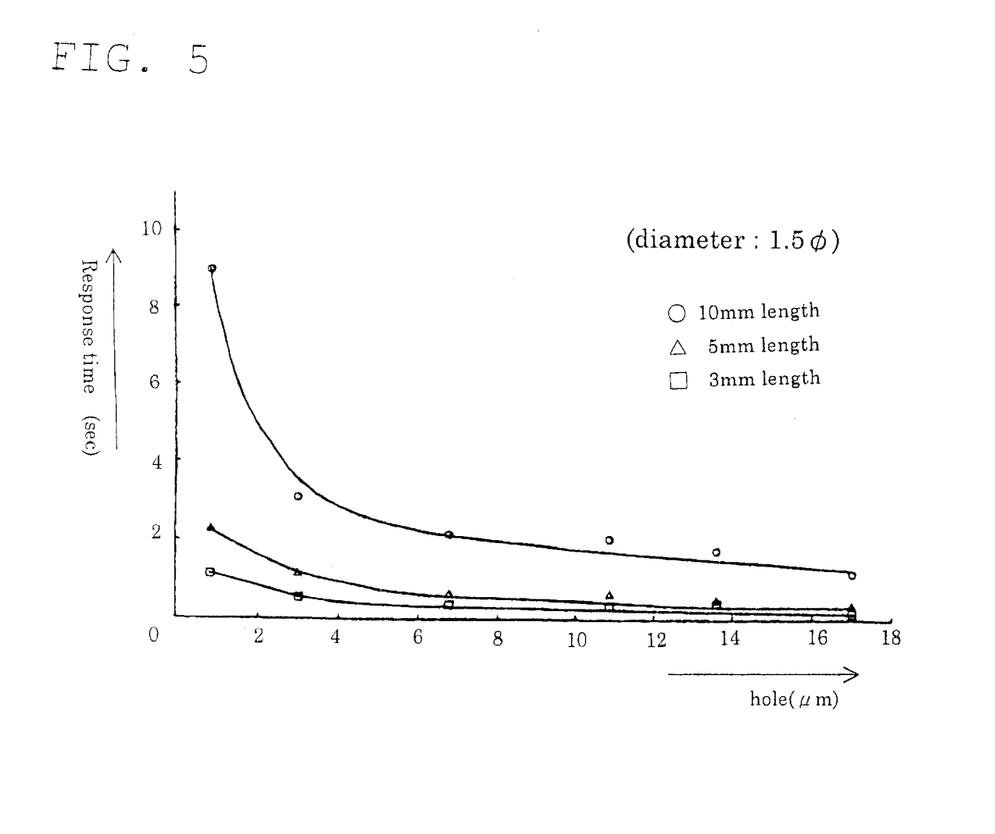
Figure 6:
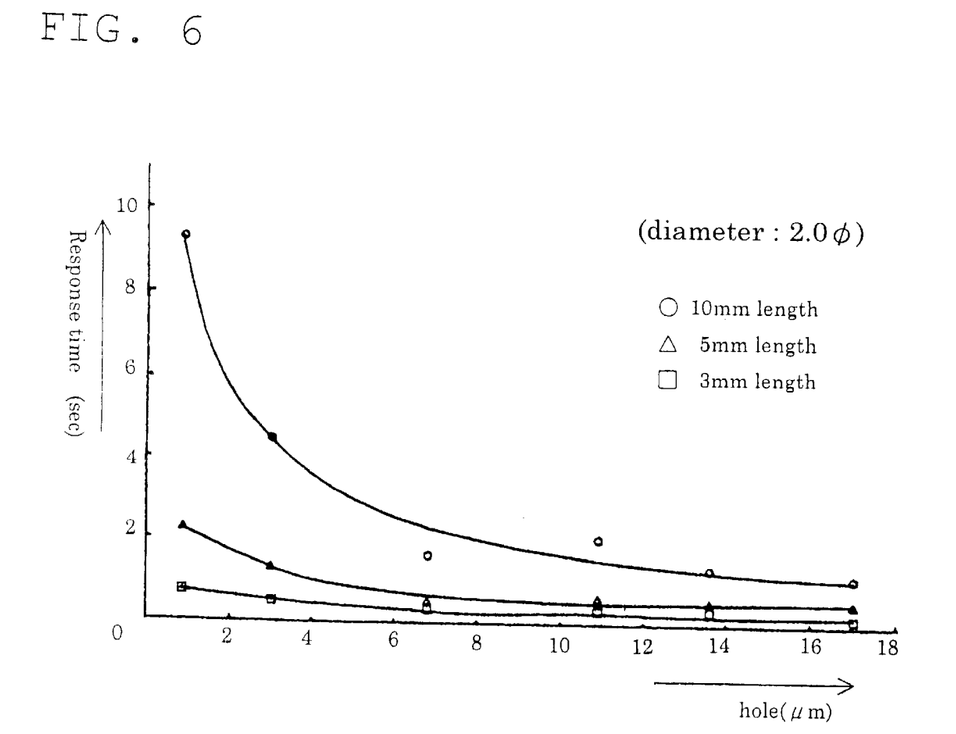

As apparent from the results shown in the figures, the diameter of the shirasu porous glass as a sample has no correlation with the response speed. The shorter the sample is, the faster the response is. The response speed is approximately constant at a pore diameter of 6 to 8 $\mu$m or more. Therefore, assuming the target body fluid is urine, it is desirable to use shirasu porous glass having a pore diameter of 6 $\mu$m or more. The distances between an end 11$a$ of a water absorber 11 and the tips 12$a$ and 13$a$ of the electrodes, respectively, may be selected appropriately.

(2) Comparative Test

Figure 7:
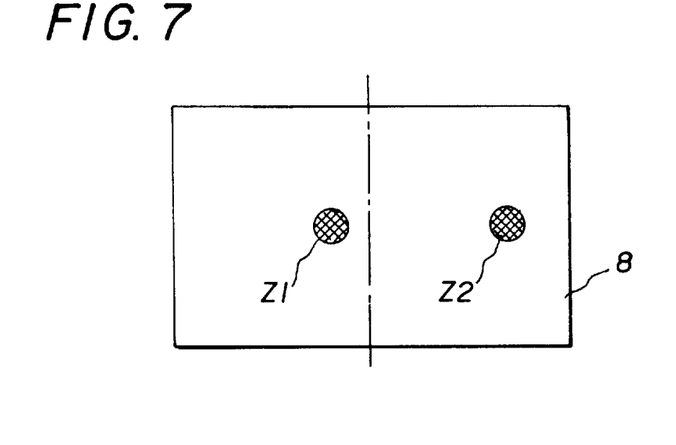
FIG. 7 is a plan view of a diaper tested in the comparative tests.
Figure 8:
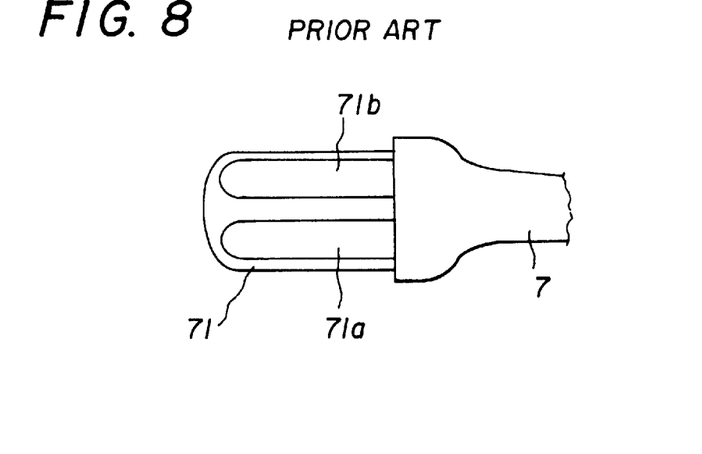
FIG. 8 is a side view showing a substrate sensor of a comparative test.
Figure 9:
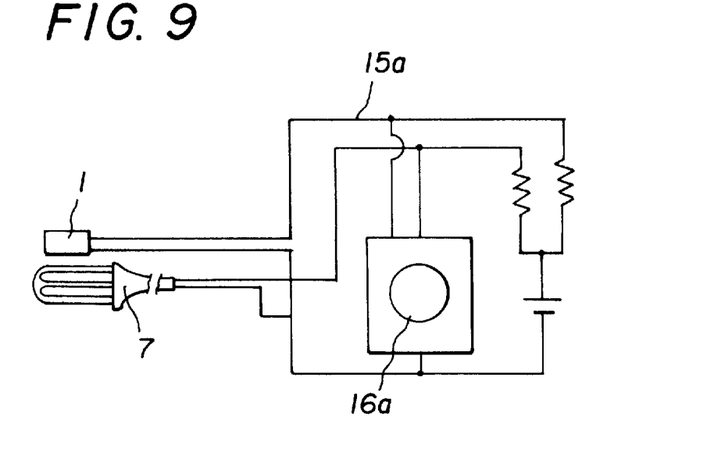
FIG. 9 is a circuit diagram of a comparative test.

A sensor 1 shown in FIG. 1 was fabricated using shirasu porous glass of 6.8 $\mu$m in pore diameter, 2 mm in diameter, and 5 mm in length. On the other hand, as shown in FIG. 8, as a comparison sensor, a substrate sensor 7 comprises a substrate 71 having mounted thereon electrodes 71$a$ and 71$b$ was fabricated. The sensor 1 and the substrate sensor 7 were fixed to point Z2 of a diaper 8 ("Silva" (trade name), flat type, manufactured by HAKUJUJI) as shown in FIG. 7 and 20 ml of artificial urine, the same as in the above response speed test, was added to point Z1. Each sensor was connected with a measuring circuit 15$a$ shown in FIG. 9, and the response speed was observed on an oscilloscope 16$a$. The response speed was observed in terms of time from the addition of the artificial urine to the response. The test was repeated five times each. The results are shown in FIG. 10.

Figure 10:
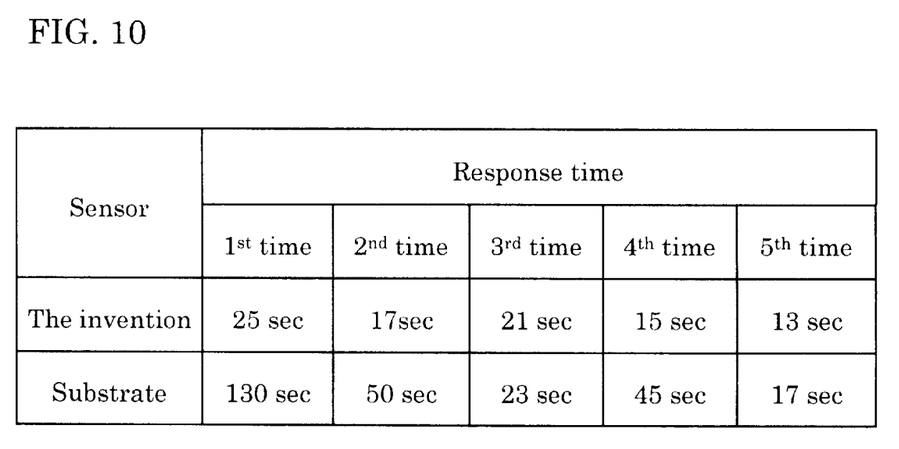
FIG. 10 is a table showing results of comparative tests.

From FIG. 10, it can be seen that the sensor 1 is faster in average response time than the substrate sensor 7 and shows little fluctuation among tests. This evidences that the sensor 1 with the shirasu porous glass is a very sensitive, stable liquid sensing sensor. This is because the substrate sensor 7 requires that both electrodes must make contact with the liquid while the sensor 1 with the shirasu porous glass can achieve the desired effect if only a single desired portion of the water absorber 11 contacts with the liquid.

EXAMPLE 2

In Example 2, a unidirectional type sensing apparatus using the sensor described in Example 1 will be described. That is, this sensing apparatus is constructed of a transmitter for transmitting a signal of the effect that the sensor senses the leakage of body fluid and a receiver for receiving the signal and making a notification.

Figure 11:
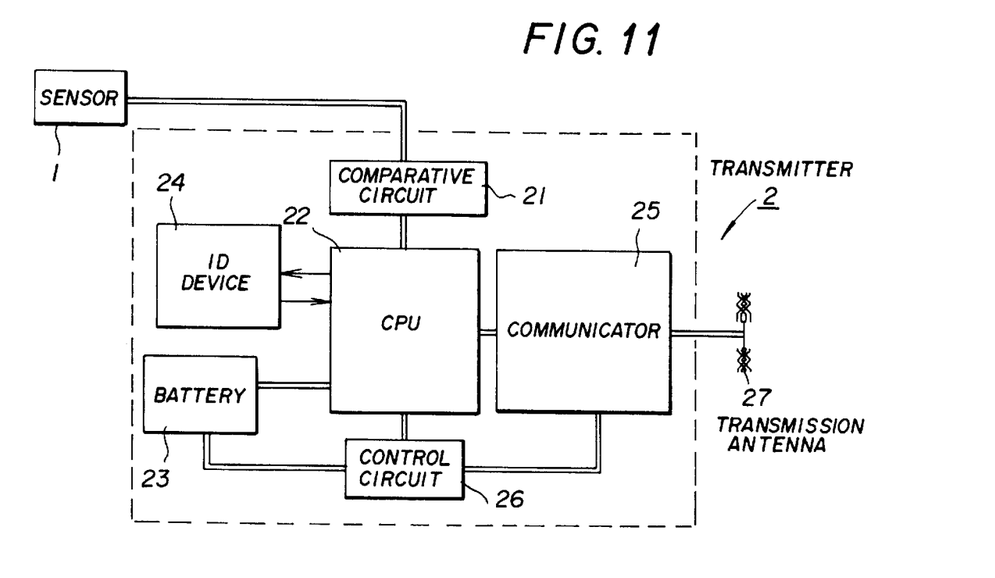
FIG. 11 is a block diagram showing a basic construction of a transmitter in the apparatus for sensing body fluid leakage of Example 2.

As shown in FIG. 11, a transmitter 2 is constructed of the sensor 1 described above, a comparative circuit 21 that judges the resistance value of the sensor 1, a CPU 22 that controls general operation of the transmitter 2, a battery 23 as a power source in the transmitter 2, an ID device 24 that outputs an individual signal of an individual transmitter 2 and a type signal of the type of device, a communicator that converts the signal from the CPU 22 to a transmission wave and oscillates it, a transmission antenna 27 for transmitting the transmission wave, a control circuit 26 for controlling the circuit between the battery 23 and the communicator 25 based on a command from the CPU 22.

Figure 12:
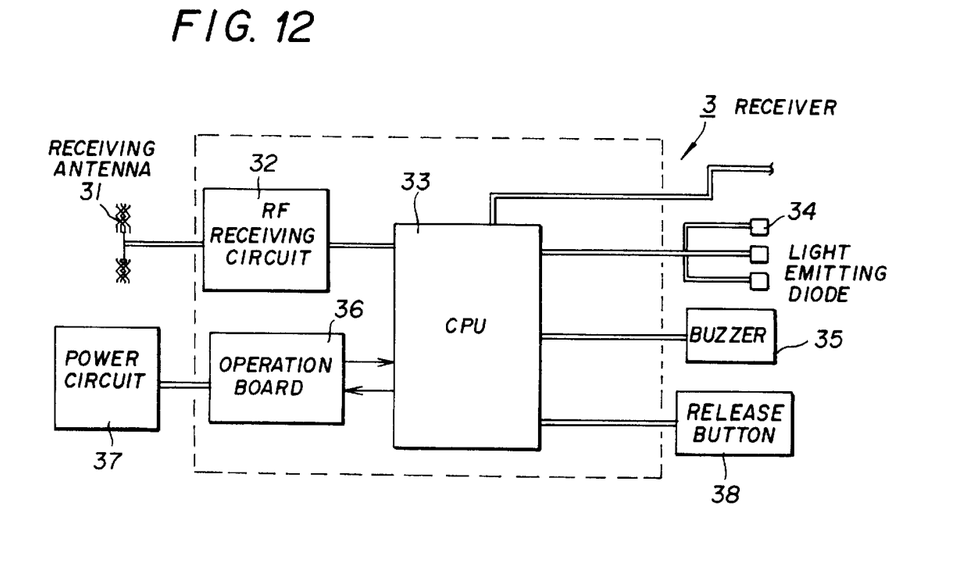
FIG. 12 is a block diagram showing a basic construction of a receiver in the apparatus for sensing body fluid leakage of Example 2.

As shown in FIG. 12, the receiver 3 is constructed by a receiving antenna 31 for receiving the signal transmitted from the communicator 2, an RF receiving circuit 32 for demodulating the received signal, a CPU 33 for processing the signal obtained by demodulation, a light emitting diode 34 that emits light by a command from the CPU 33 and a buzzer 35 that generates sound, serving as notifying means, an operation board 36 for performing setting of an ID in the operation of the notifying means, or the like, a power circuit 37 for supplying power to the receiver 3, and a release button 38 that releases the operation of the notifying means. The CPU 33 is connected with other notifying means (not shown) in a nurse center, etc. as a parallel means for the notifying means. A plurality of light emitting diodes 34 are arranged such that the operation of the CPU 33 based on the ID set through the operation board 36 can identify the communicator that has made notification.

Here, a further specific mode of attachment will be shown.

Figure 14:
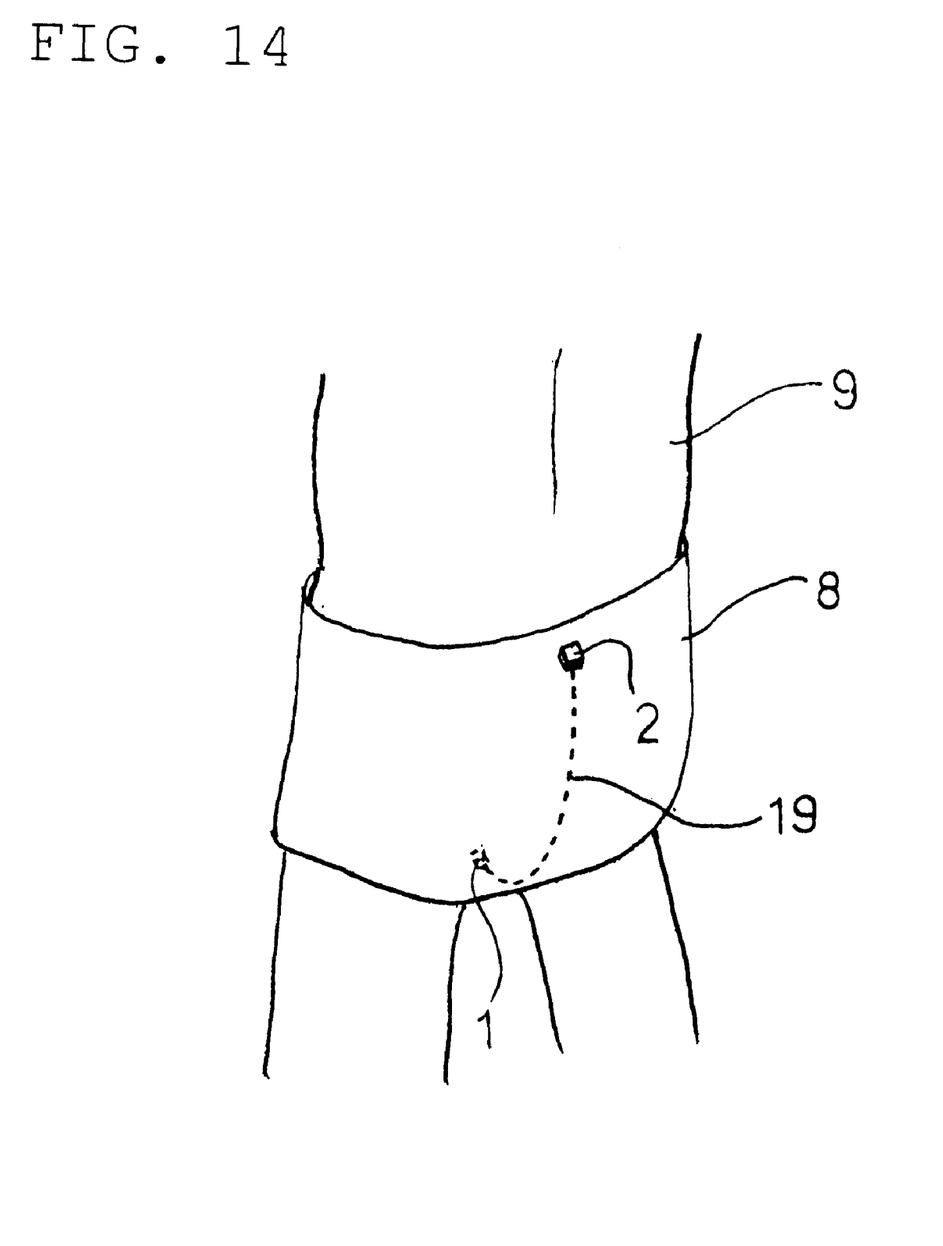
FIG. 14 is a schematic diagram illustrating the manner of use of the apparatus for sensing body fluid leakage of Example 2.

As shown in FIG. 14, the transmitter 2 has an integrated circuit that includes all the components other than the sensor 1 in a compact construction. The integrated circuit is put in a case (not shown) of a water-proof structure. The sensor 1 is detachably connected with the transmitter 2 through a lead wire 19 of a redetermined length. When a diaper 8 is attached to a person under care 9, the sensor 1 is arranged so as to be positioned near the urination site. The transmitter 2 is recommended to be fixed on an upper part, etc., of the diaper 8 by a pressure-sensitive adhesive tape, etc. The sensor 1 can be made as a throwaway type one. Accordingly, the sensor 1 may be incorporated in advance in the inside of the diaper 8 when the diaper 8 is fabricated, with separately setting designs for male and female users when the diaper 8 is a paper diaper. In the case of a diaper for male users, the sensor 1 is set so as to be positioned near the penis and it is set so as to be positioned near the vagina in the case of a diaper for female users. With this construction, when the diaper is exchanged, only exchanging the jack of the sensor 1 can reset the transmitter 2 without difficulty. The sensor 1 does not contact the skin of the user so that the user will not feel uneasy.

Figure 13:
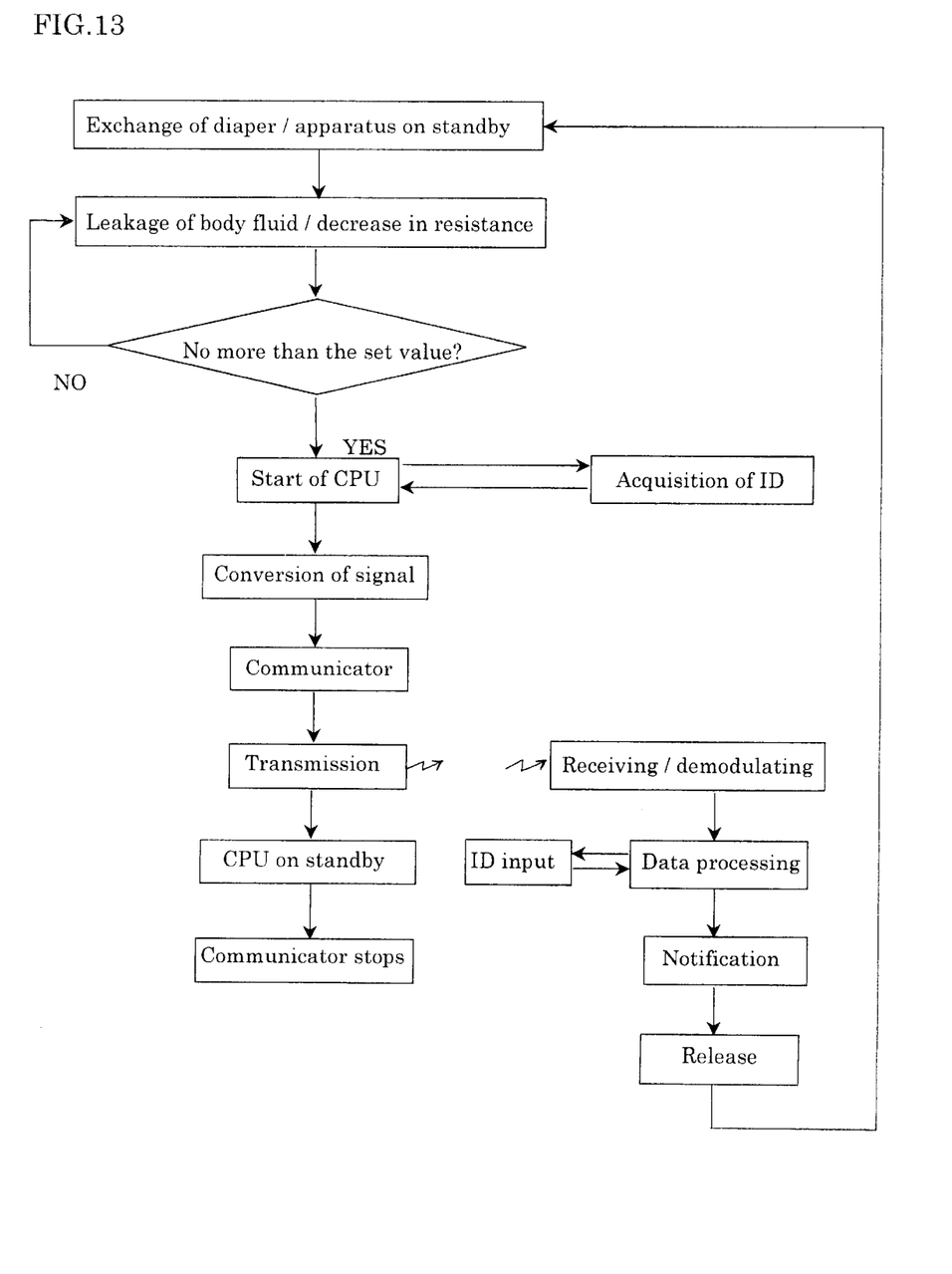
FIG. 13 is a flowchart illustrating the operation of the apparatus for sensing body fluid leakage of Example 2.

Next, the operation of the whole sensing apparatus will be described based on the flowchart in FIG. 13 with reference to FIGS. 11 and 12.

(1) The transmitter 2 attached to the body of a user in the above-described manner is on standby until urination occurs.

(2) When urination occurs, the sensor 1 senses it and the resistance decreases. As a result of the decrease, current flows in the comparative circuit 21. In the comparative circuit 21, a resistance value is set in advance as a threshold value. When the resistance value corresponding to the current which flows is no higher than the set resistance value, it recognizes the occurrence of the leakage of body fluid and outputs a signal to that effect to the CPU 22. When the resistance value corresponding to the current which flows is higher than the set resistance value, it does not output a signal until the resistance value becomes equal to or lower than the set value. In the instant example, in order to recognize differences between urine and water, the resistance value as a threshold value is set to 400 Ω.

(3) When the signal is input to the CPU 22 from the comparative circuit 21, the CPU 22 comes out of standby and starts operation, acquiring an individual signal and device type signal from the ID device 24, outputting sensed signal, individual signal and device type signal to the communicator 25, and at the same time operating the control circuit 26 to start the communicator 25.

(4) The communicator 25 converts each inputted signal to a transmission wave and transmits it to the receiver 3. The operation of the receiver 3 will be described later.

(5) When it recognizes transmission of a signal by the communicator 25, the CPU 22 is placed on standby again, the current is cut by the control circuit 26 and the operation of the communicator 25 is terminated.

(6) On the other hand, the receiver 3 that has received the signal demodulates it by the RF receiving circuit 32 and inputs it as data to the CPU 33.

(7) The CPU 33 to which the data has been inputted processes it with the set ID, etc. by the operation board in advance and performs notification to the outside by necessary notification means depending on the results.

(8) The person who received the notification confirms which communicator 2 has sent the notification and then releases the notification by the release button 38.

(9) The person who released the notification goes to the person under care or patient who wears the transmitter 2 and exchanges the diaper. In this case, the sensor 1 is pulled from the comparative circuit 22 and exchanged by a new sensor 1. This resets the comparative circuit 22 and places it on standby until the next leakage of body fluid is sensed.

In the setting of the comparative circuit 22 in the instant example, the resistance value as a threshold value is set to 400 Ω. However, the threshold value is not limited to this value but various elements, for example, a difference in resistance value in comparing sweat and urine, a difference in resistance value between sweat and blood, or a variation of resistance value accompanying a variation in temperature, may be set in advance as comparative elements so that the leakage of body fluid can be sensed depending on the purpose.

EXAMPLE 3

In the instant example, an explanation will be made of a bi-directional type body fluid leakage sensing apparatus that transmits and receives signals bi-directionally between a transmitter-receiver on the sensor side using the sensor described in Example 1 and a transmitter-receiver on the notification side and performs notification.

The apparatus includes a transmitter-receiver on the sensor side of the instant example (hereinafter, referred to as "sensing communicator 4") and a transmitter-receiver on the communicator side that receives a signal to the effect that the leakage of body fluid is sensed from the sensing communicator 4 (hereinafter, referred to as "notifying communicator 5").

Figure 15:
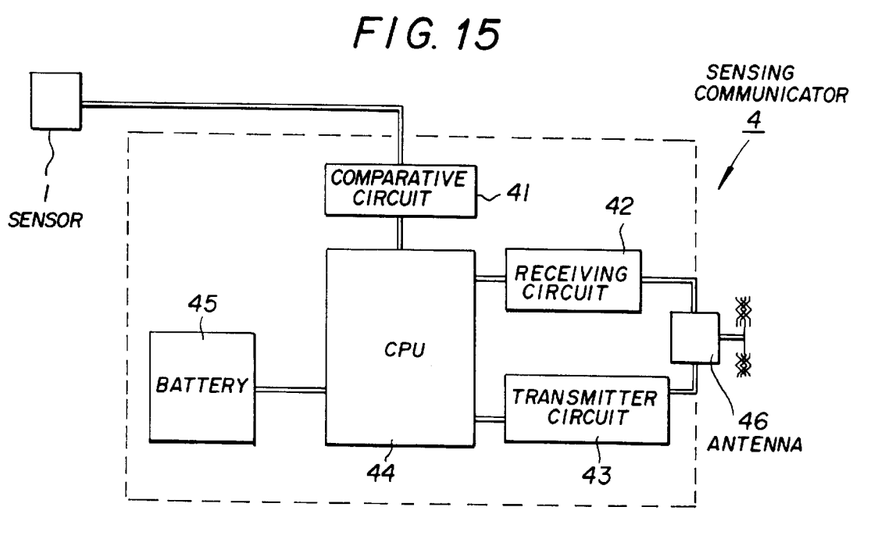
FIG. 15 is a block diagram showing the basic construction of a sensing communicator of the apparatus for sensing body fluid leakage of Example 3.

As shown in FIG. 15, the sensing communicator 4 includes the above-described sensor 1, a comparative circuit 41, a receiving circuit 42 that receives a command from the notifying communicator 5, a transmitter circuit 43 that transmits data to the notifying communicator 5, a CPU 44 that processes the command from the notifying communicator 5 and a signal from the comparative circuit 41 and outputs data to the transmitter circuit 43, a battery 45 as a power source of the sensing communicator 4, and an antenna portion 46 associated with transmitting and receiving between the receiving circuit 42 and the transmitter circuit 43.

Figure 16:
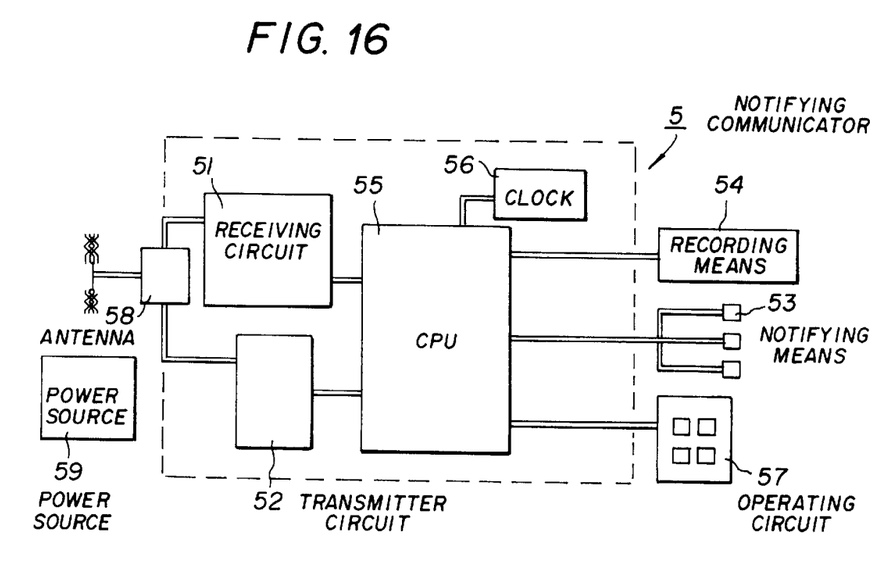
FIG. 16 is a block diagram showing the basic construction of a notifying communicator of the apparatus for sensing body fluid leakage of Example 3.
Figure 17:
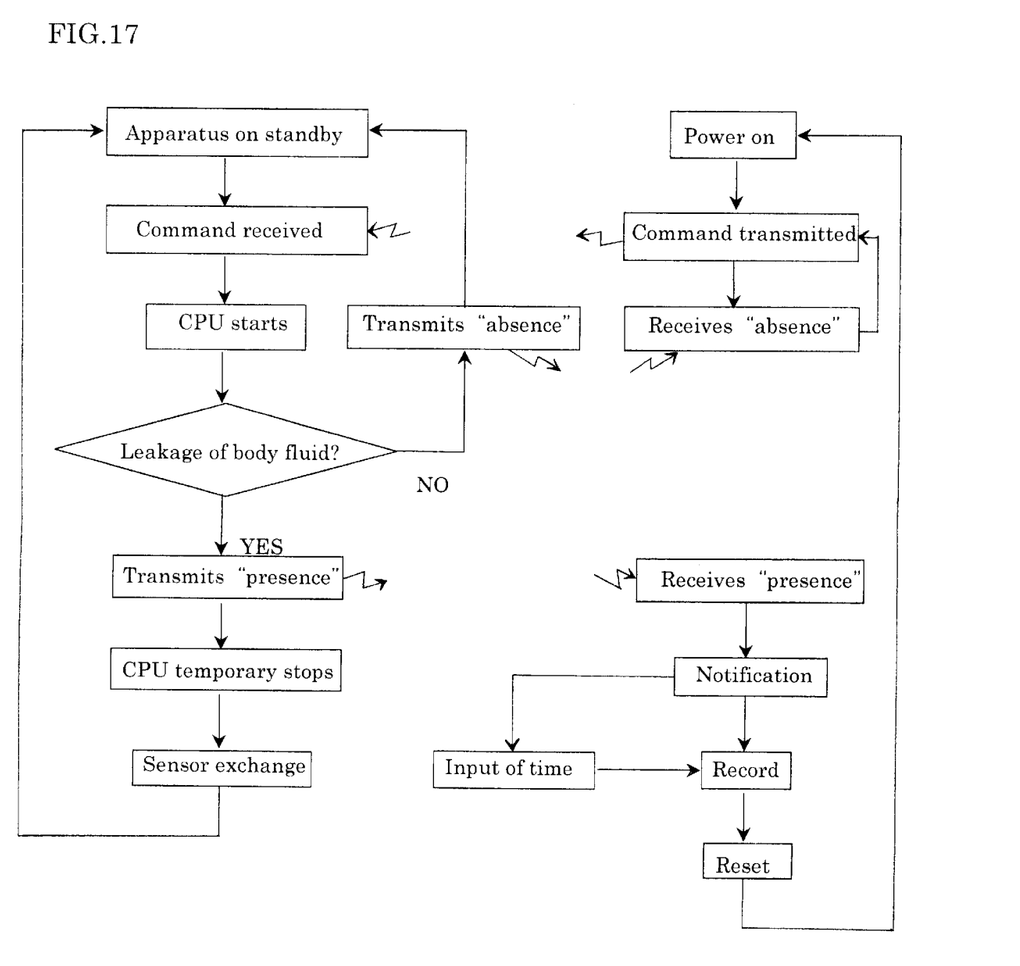
FIG. 17 is a flowchart illustrating the operation of the apparatus for sensing body fluid leakage of Example 3.

On the other hand, as shown in FIG. 16, the notifying communicator 5 includes a receiving circuit 51 that receives data From the sensing communicator 4, a transmitter circuit 52 that transmits a command to the sensing communicator 4, a notifying means 53 that notifies sensing of the leakage of body fluid, a recording means 54 that records sensing of the leakage of body fluid, a CPU 55 that performs various data processing and outputs a command, a clock 56 that outputs time information to the CPU 55, an operating circuit 57 that performs ID setting, etc. and sends that information to the CPU 55, an antenna portion 58 that relates to transmission and reception, and a power source portion 59.

Next, an explanation will be made of the operation of the bi-directional type liquid sensing apparatus based on the flowchart with reference to FIGS. 15 and 16.

I) Like the transmitter 2 in Example 2, it is on standby when the sensing communicator 4 is attached to the person under care. As for the notifying communicator 5, when the power is turned on, the CPU 55 produces a command and transmits it to the sensing communicator 4 through the transmitter circuit 52.

II) The sensing communicator 4, which received the command from the receiving circuit 42, starts the CPU 44 and requests the comparative circuit 41 for the presence or absence of sensing. The comparative circuit 41 compares the resistance value of the sensor 1 with the preset value.

III) When the result is "no leakage of body fluid," the CPU 44 transmits data to that effect to the notifying communicator 5 through the transmitter circuit 43 and at the same time it is placed on standby again.

IV) When the CPU 44 is started by the command and the comparative circuit 41 judges that "leakage of body fluid is present," then the CPU 44 transmits data to that effect to the notifying communicator 5 and falls into a temporary dormant state.

V) The CPU 55 that received the data from the receiving circuit 52 judges whether "the leakage of body fluid is present or absent." When the judgment is "absent," the CPU 55 transmits this to the notifying means 52 and outputs a next command after a while.

VI) When the judgment is "present," the CPU 55 outputs a signal to the notifying means 53 to notify the caregiver by means of light emission or sounding, and at the same time incorporates the time information from the clock 56 and then combines this with the signal of "the leakage of body fluid is present" and outputs the signal to the recording means 54 to record the signal together with time.

VII) The caregiver who received the notification of "the leakage is present" resets the notifying means 53 and thereafter goes to the person under care or patient concerned and exchanges the sensor 1 together with the diaper. This resets the sensing communicator 4 and is now in a state where it can be restarted upon receipt of a command.

The caregiver, who takes with him or her a portable device provided with a receiving function and a notification means, can instantaneously recognize the fact that sensing of leakage of body fluid has occurred so that he or she can confirm which person under care the notification is from by means of the notifying communicator as the main body.

Since it is constituted as described above, the present invention has the following excellent effects.

(1) A sensor that senses a liquid at high sensitivity can be constructed by a simple structure so that the sensor is useful as a sensor for sensing the leakage of body fluid such as incontinence as a throwaway sensor.

(2) By applying the above sensor, a highly reliable body fluid leakage sensing apparatus can be constructed.

(3) By use of highly accurate sensor and body fluid leakage sensing apparatus, the labor of caregivers can be reduced.

Industrial Applicability

As described above, the liquid sensing sensor and the apparatus for sensing body fluid leakage using the same according to the present invention enable caregivers to quickly recognize incontinence by a person under care. Then, it can contribute to reduction of labor of caregivers and to a comfortable life of persons under care in care facilities for aged person or hospitals. By modifying the mode of use, the sensor and apparatus are useful as medical goods such as an apparatus for sensing bleeding after surgery and find high applicability.

What is claimed is:

1. A liquid sensing sensor, comprising a water absorber made of a porous material having high electric resistance which is provided on a head of the sensor, at least two electrodes having respective tips arranged separate from each other through the water absorber but fixed to the water absorber respectively, and a coating means for covering the water absorber and the tips, wherein the porous material is porous glass calcined from volcanic fallen ash or sand as a main raw material.

2. The liquid sensing sensor as claimed in claim 1, characterized in that the coating means covers the tips of electrodes and coats the water absorber so that a portion of the water absorber is exposed.

3. The liquid sensing sensor as claimed in claim 1, characterized in that the porous material has a pore diameter of 0.1 to 50.0 $\mu$m.

4. The liquid sensing sensor as claimed in claim 3, characterized in that the porous material has a pore diameter of 6 to 50.0 $\mu$m.

* * * * *

UNITED STATES PATENT AND TRADEMARK OFFICE
CERTIFICATE OF CORRECTION

PATENT NO. : 6,433,695 B1
DATED : August 13, 2002
INVENTOR(S) : Kazuo Kai et al.

It is certified that error appears in the above-identified patent and that said Letters Patent is hereby corrected as shown below:

<u>Title page,</u>
Item [86], "§ 371 (c)(1), (2), (4) Date: August 4, 1999" should read -- § 371 (c)(1), (2), (4) Date: August 4, 2000 --.

Signed and Sealed this

Fifteenth Day of October, 2002

*Attest:*

*Attesting Officer*

JAMES E. ROGAN
*Director of the United States Patent and Trademark Office*